US012343195B2

(12) United States Patent
Choudhury et al.

(10) Patent No.: US 12,343,195 B2
(45) Date of Patent: Jul. 1, 2025

(54) SYSTEM AND METHOD OF GENERATING IMAGE OF VASCULAR FLOW NETWORK

(71) Applicant: Neurasignal, Inc., Los Angeles, CA (US)

(72) Inventors: Asutosh Choudhury, Bhubaneswar (IN); Sivasankaran Krishnan, Bengaluru (IN); Vivekanand Balakrishnan, Bengaluru (IN); Ajay Zachariah, Mercer Island, WA (US); Madala Naveen Raghuveer, Vinukonda (IN); Heming Wu, Sacramento, CA (US); Shankar Radhakrishnan, Los Angeles, CA (US); Naresh Sehgal, Santa Clara, CA (US)

(73) Assignee: Neurasignal, Inc., Los Angeles, CA (US)

( * ) Notice: Subject to any disclaimer, the term of this patent is extended or adjusted under 35 U.S.C. 154(b) by 313 days.

(21) Appl. No.: 17/862,245

(22) Filed: Jul. 11, 2022

(65) Prior Publication Data

US 2023/0329668 A1  Oct. 19, 2023

(51) Int. Cl.
  *A61B 8/06* (2006.01)
  *A61B 8/00* (2006.01)
  *A61B 8/08* (2006.01)

(52) U.S. Cl.
  CPC ............... *A61B 8/06* (2013.01); *A61B 8/488* (2013.01); *A61B 8/0891* (2013.01)

(58) Field of Classification Search
  CPC .......... A61B 8/06; A61B 8/488; A61B 8/0891
  See application file for complete search history.

(56) References Cited

U.S. PATENT DOCUMENTS

| | | | | |
|---|---|---|---|---|
| 4,205,687 | A * | 6/1980 | White ................. | A61B 8/06 600/455 |
| 2006/0262968 | A1* | 11/2006 | Drobnitzky .......... | G06T 11/008 382/128 |
| 2011/0137175 | A1* | 6/2011 | Hossack ............... | A61B 8/488 600/454 |
| 2015/0141832 | A1* | 5/2015 | Yu ....................... | G01S 7/52085 600/455 |
| 2021/0106305 | A1* | 4/2021 | Wang ................... | A61B 8/466 |
| 2023/0341548 | A1* | 10/2023 | Levi .................... | A61B 8/4227 |

* cited by examiner

*Primary Examiner* — Anne M Kozak
*Assistant Examiner* — Brooke Lyn Klein
(74) *Attorney, Agent, or Firm* — Polygon IP, LLP

(57) ABSTRACT

A method and system for monitoring ultrasound tests and generating images to visually summarize the test results, are described. The method includes receiving ultrasound test data representing blood flow in a blood vessel of several interconnected blood vessels of a brain, and determining, based on the ultrasound test data, a direction and one or more hemodynamic values at a location in the blood vessel. An image of the interconnected blood vessels of the brain is generated. The image includes a direction indicator corresponding to the direction and a hemodynamic indicator corresponding to the one or more hemodynamic values. A user may view the image to assess whether the blood flow in the blood vessel is normal. Other embodiments are also described and claimed.

20 Claims, 8 Drawing Sheets

402

| VESSEL | MEAN (CM/S) | DEPTH (MM) | PI | EDV (CM/S) | PSV (CM/S) | TIME |
|---|---|---|---|---|---|---|
| MCA | 74 | 39 | 0.99 | 48 | 121 | 12:11:27 PM |
| MCA | 75 | 42 | 1.00 | 49 | 124 | 12:11:19 PM |
| ACA | -32 | 67 | 1.08 | -20 | -55 | 12:10:02 PM |
| ACA | | | | | | |
| PCA | 43 | 65 | 0.95 | 27 | 68 | 12:13:10 PM |
| ICA | -25 | 51 | 1.31 | -14 | -47 | 12:15:11 PM |
| LINDEGAARD RATIO: 3.00 | | | | | | |

| IMAGE   VIDEO   DETAILS | |
|---|---|
| VESSEL | LMCA |
| DEPTH | 50 MM |
| MEAN | 85 CM/S |
| PI | 0.792 |
| MAX | 124 CM/S |
| MIN | 57 CM/S |
| POWER | 100 |

8/9 [PREVIOUS] [NEXT]

SYSTEM AND METHOD OF GENERATING IMAGE OF VASCULAR FLOW NETWORK

CROSS-REFERENCE TO RELATED APPLICATIONS

The present application claims priority to and the benefit of Indian Patent Application No. 202221022695, filed on Apr. 18, 2022, the disclosure of which is hereby incorporated by reference in its entirety.

BACKGROUND

Field

The present disclosure relates to systems and methods of generating images of vascular flow networks to visualize ultrasound test results and, more specifically, systems and methods for generating images of blood vessels in a brain to visualize transcranial Doppler ultrasound test results.

Background Information

Ultrasound imaging is used in medicine to non-invasively examine the health and function of the human body. For example, transcranial Doppler (TCD) can be used to measure the velocity of blood flow in a neurovasculature of a patient. Currently, TCD ultrasound examinations are typically performed by a sonographer using a transducer of a TCD ultrasound machine to identify and insonate a region of vasculature. Echoes of ultrasound waves insonating the region of vasculature are received and analyzed by the TCD ultrasound machine, and the test results are displayed on the TCD ultrasound machine for observation by the sonographer. Blood flow measurements and/or screen captures and videos taken during the examination may be stored for later review by a medical practitioner, e.g., in a multi-page report. The medical practitioner may review the multi-page report to diagnose aneurysms, vasospasms, and other health problems of the patient.

SUMMARY

Existing transcranial Doppler (TCD) ultrasound machines can be used by medical practitioners to view ultrasound test results concurrently with the test, or afterward, through multi-page reports that include tabulated blood flow measurements. For example, the medical practitioner may peruse the tabular report to review blood flow velocity readings taken for different vessels. The tabulated readings, however, do not allow the medical practitioner to efficiently assess the blood flow of the patient in a visual manner, nor do the tabulated readings allow the medical practitioner to quickly assess whether such blood flow is normal. Accordingly, there is a need for an ultrasound test monitoring system that generates images based on ultrasound test data to allow a medical practitioner to efficiently assess blood flow in a blood vessel. For example, medical practitioners would benefit from images that indicate a direction and/or hemodynamic value of blood flow at a location within interconnected blood vessels of the brain, e.g., within a circle of Willis.

A method of generating images of blood vessels in a brain is provided herein. In an embodiment, an ultrasound test monitoring system receives ultrasound test data, e.g., from a TCD ultrasound machine. The ultrasound test data includes data representing blood flow in a blood vessel of interconnected blood vessels of a brain. For example, the interconnected blood vessels can include a circle of Willis in the brain, and the blood vessel can be a medial cerebral artery of the circle of Willis. The system can determine, based on the ultrasound test data, a direction and one or more hemodynamic values of the blood flow at a location in the blood vessel. For example, the system can determine that the blood is flowing in a distal direction and has a mean velocity of a particular value within a proximal, medial, or distal segment of the cerebral artery. Additionally, the system may determine a depth of the location relative to an ultrasound probe used to collect the ultrasound test data. Accordingly, the system can determine information about the blood flow within one or more segments of each vessel of the circle of Willis.

In an embodiment, the system can generate an image of the interconnected blood vessels, and the image can include annotations detailing the direction and hemodynamic values determined by the system. For example, the image can be a 2D image or a 3D image of the circle of Willis, and direction indicators corresponding to the direction, as well as hemodynamic indicators corresponding to the hemodynamic values can be overlaid on or appended to the image. The image may also include depth indicators corresponding to the depths of the locations at which each of the direction and hemodynamic values were measured. Accordingly, a medical practitioner can view the image and quickly ascertain whether the blood flow in the circle of Willis is normal.

Normality of the blood flow may be indicated by the generated image. More particularly, the image can alert the medical practitioner to any abnormalities. For example, an orientation of the direction indicator in the image may change when the direction of blood flow is abnormal. Similarly, a color of the hemodynamic indicator in the image may change when the hemodynamic value is abnormal. Normality of the indicators can be determined relative to predetermined values, e.g., based on expected flow directions or ranges of normal flow velocities known from historical data. The historical data can be collected from a patient being examined or other patients in a general population. Accordingly, the medical practitioner can assess the blood flow health based on historically determined normal ranges.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Embodiments describe a system and method of generating images of blood vessels in a brain to visualize ultrasound test results. The system and method can be used to visually summarize the test results for a medical practitioner that is not present at a transcranial Doppler (TCD) ultrasound test, for example. However, the system and method may also be used to visually summarize other ultrasound or medical imaging tests. Thus, reference to the system as being used for any particular medical test is not limiting.

In an aspect, a system and method of generating images of blood vessels in a brain to visually summarize ultrasound test results, is provided. The system and method can generate a single image mapping key hemodynamic information to locations of an anatomical structure, such as by overlaying a direction and/or a hemodynamic value of blood flow on a blood vessel. The blood vessel can be part of an interconnected network of blood vessels, such as the circle of Willis in the brain, and hemodynamic information for the network of blood vessels can be overlaid at respective locations in the network of blood vessels in the image. More particularly, 2D and 3D images of the circle of Willis having annotated values corresponding to measured and calculated hemodynamic values from a TCD exam, e.g., mean velocity, vessel name, blood flow, Lindegaard ratio, and pulsatility index, can be generated for display on a user device. Accordingly, a medical practitioner can view the images on a user device to clearly visualize and efficiently ascertain the blood flow health of a patient through a single view, and may share the visualization to explain the hemodynamics of the brain to medical and non-medical personnel.

Figure 1:
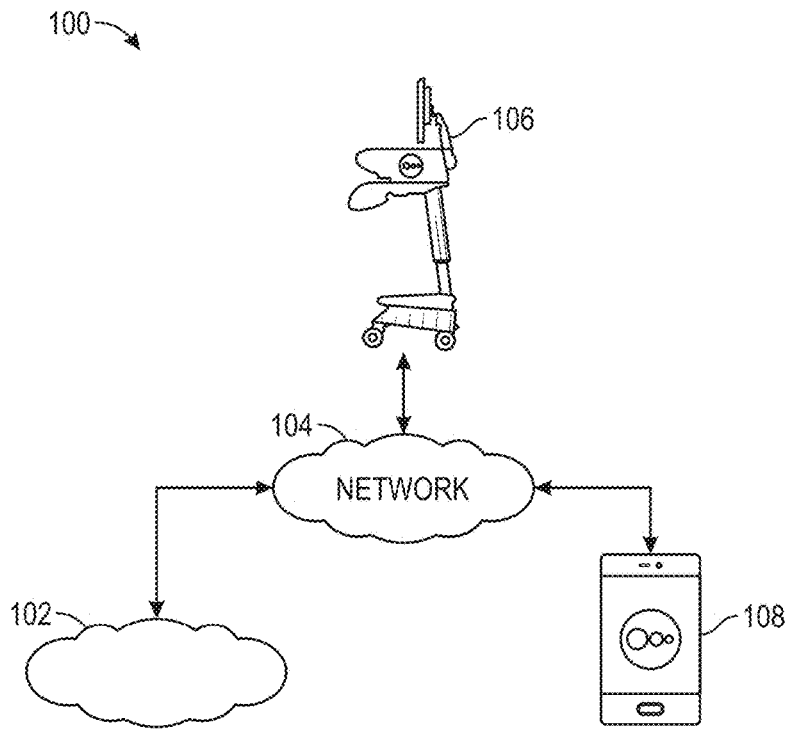
FIG. 1 is a block diagram of an example environment for monitoring ultrasound tests, in accordance with an embodiment.

Referring to FIG. 1, a block diagram of an example environment for monitoring ultrasound tests is shown in accordance with an embodiment. As shown, the environment 100 includes an ultrasound test monitoring system 102 that is interconnected with one or more other devices via a communications network 104. The communications network 104 may be the internet, a wide area network (WAN), intranet, or other suitable network. The ultrasound test monitoring system 102 may be hosted on one or more local servers, may be a cloud based system, or may be a hybrid system with local servers and in the cloud. The ultrasound test monitoring system 102 is maintained by engineers which develop features and tools, such as a front-end user interface having account views to set up predetermined normal ranges of blood flow characteristics, which may be used to evaluate hemodynamic values of blood flow, as described below.

In an embodiment, the environment 100 is a distributed system in which the ultrasound test monitoring system 102 is connected to a TCD ultrasound machine 106 and a user device 108. The TCD ultrasound machine 106 is used to conduct a TCD ultrasound examination of a patient. The TCD ultrasound machine 106 can transmit live data of the examination to the ultrasound test monitoring system 102 via a computer communications protocol. It will be appreciated that the TCD ultrasound machine 106 is a non-limiting example of medical devices that can interact with the test monitoring system and that other medical devices, such as electrocardiogram (EKG) machines, can also be used. The ultrasound test monitoring system 102 can generate, based on the test data, images that visually summarize the test data. The images may be transmitted to the user device 108, which may be used by a medical practitioner. The images may be displayed on a display of the user device 108 to allow the medical practitioner to efficiently assess the test data and determine whether the blood flow of the patient is normal.

Although FIG. 1 shows only a select number of computing devices and/or systems (e.g., one ultrasound test monitoring system 102, one TCD ultrasound machine 106, and one user device 108), the environment 100 may include any number of computing devices and/or systems that are interconnected in any arrangement to facilitate the exchange of data between the computing devices and/or systems.

Figure 2:
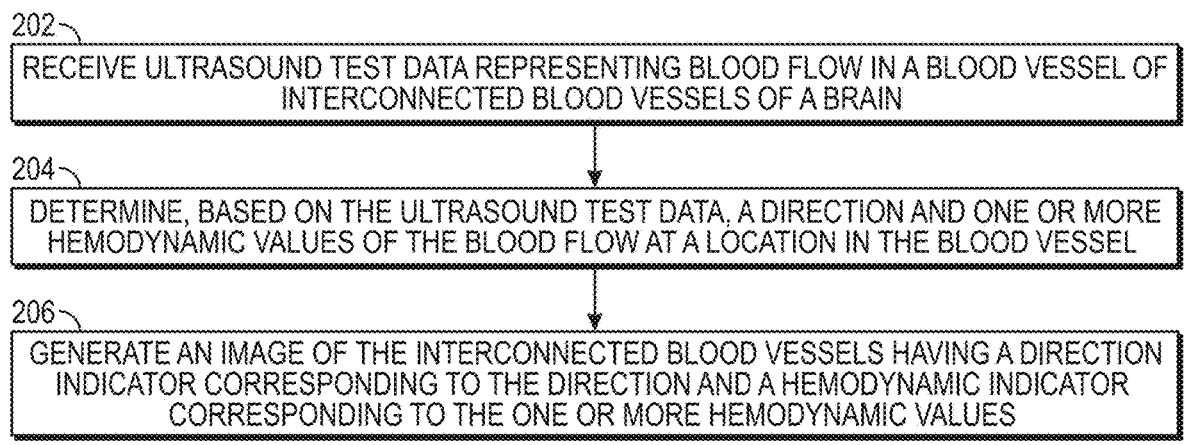
FIG. 2 is a flowchart of a method of generating images of blood vessels in a brain, in accordance with an embodiment.

The ultrasound test monitoring system 102 integrates several components that allow for the receipt of ultrasound test data and the generation of images of interconnected blood vessels of the brain. More particularly, the ultrasound test monitoring system 102 includes components that are configured to perform the method illustrated in FIG. 2. Furthermore, operations of the method of generating images as shown in FIG. 2 are illustrated in FIGS. 3-10. Accordingly, the components of the ultrasound test monitoring system 102 shown in FIG. 1 and the operations of FIG. 2 shall be referred to and described in more detail within the description of the figures that follows.

Figures 3, 4:
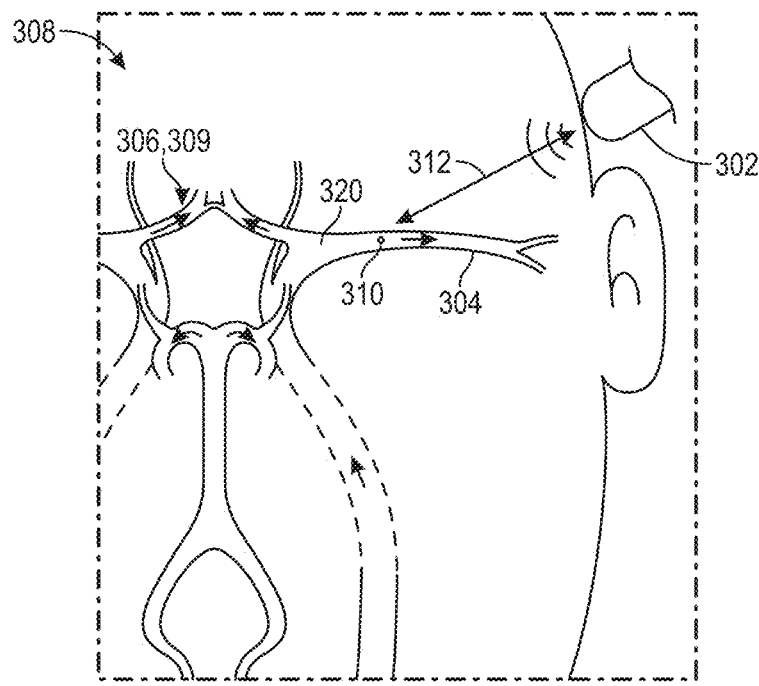
FIG. 3 is a pictorial view of a transcranial Doppler (TCD) ultrasound examination of blood vessels in a brain, in accordance with an embodiment.
FIG. 4 is a pictorial view of tabulated TCD test data, in accordance with an embodiment.

Referring to FIG. 3, a pictorial view of a transcranial Doppler (TCD) ultrasound examination of blood vessels in a brain is shown in accordance with an embodiment. At operation 202, the ultrasound test monitoring system 102 receives ultrasound test data from the TCD ultrasound machine 106. The ultrasound test data can be generated by a transducer of an ultrasound probe 302 of the TCD ultrasound machine 106, and can represent blood flow in a blood vessel 304 of interconnected blood vessels 306 of the brain 308. For example, the interconnected blood vessels 306 can include a circle of Willis 309 of the brain 308. The circle of Willis 309 is a vascular structure where several arteries within the brain join. At the circle of Willis 309, the internal carotid arteries branch into smaller arteries that supply oxygenated blood to more than 80% of the cerebrum. Accordingly, blood flow within the circle of Willis 309 and its constituent vessels is important to blood flow health. The ultrasound probe 302 can insonate the constituent blood vessels of the circle of Willis 309, e.g., a medial cerebral artery or a basilar artery, to detect blood flow therein.

The ultrasound probe 302 can detect blood flow in various locations within the blood vessel 304. The probe can emit an ultrasonic signal toward the blood vessel 304, and a reflected portion of the signal can return to, and be received by, the probe. Based on the reflected signal, the TCD ultrasound machine 106 can determine blood flow characteristics at the location 310 in the blood vessel 304. For example, the TCD ultrasound machine 106 can determine a mean velocity of the blood flow at the location 310, a pulsatility index of the blood flow at the location 310, or other hemodynamic metrics. The TCD ultrasound machine 106 may also determine a depth 312 to the location 310 from the ultrasound probe 302 used to generate the ultrasound test data. For example, the depth 312 may be a distance from an outer surface of a patient's head (which the ultrasound probe 302 is pressed against) to the location 310 within the blood vessel 304. As described below, the TCD ultrasound machine 106 can generate the ultrasound test data that is used to annotate images that summarize the TCD ultrasound examination.

Referring to FIG. 4, a pictorial view of tabulated TCD test data is shown in accordance with an embodiment. Ultrasound test data 402 may be tabulated for review by a medical practitioner. The test data can indicate a type of the blood vessel 304, e.g., a medial cerebral artery, and a mean velocity of blood flow at a location 310 in the blood vessel. The test data can also indicate the depth 312 to the location 310 from the ultrasound probe 302. The test data can indicate other hemodynamic values, such as end diastolic velocity or peak systolic velocity of the blood flow at the location 310. As shown, several locations 310 along the blood vessel 304 may be probed and measured at different times, and each measurement may be tabulated for assessment. It will be appreciated that, even when only two measurements are taken within the target blood vessel 304, the tabulated data can be difficult to digest. For example, a maximum mean velocity in the blood vessel 304 must be searched for and can be difficult to recognize when many different measurements are listed. Recognizing such metrics may be critical to accurate diagnosis, however. More particularly, metrics such as the maximum blood flow velocity in the blood vessel 304 are predictive of the likelihood of disease states, such as whether hemorrhage, stroke, or vasospasm of the blood vessel is likely.

At operation 204, when the ultrasound test data 402 is transmitted from the TCD ultrasound machine 106 to the ultrasound test monitoring system 102 during or after the exam is conducted, the system can determine, based on the ultrasound test data 402, one or more hemodynamic characteristics of the blood flow at the location 310 in the blood vessel 304. More particularly, the ultrasound test monitoring system 102 can determine a direction of the blood flow and/or one or more hemodynamic values of the blood flow at the particular location.

In an embodiment, the ultrasound test monitoring system 102 determines the location 310 based on the maximum mean velocity measured for a particular vessel. For example, referring again to FIG. 4, the maximum mean velocity measured for the medial cerebral artery is 75 cm/s, at the depth of 42 mm. At that location, the direction of flow is distal (flowing away from the heart) as indicated by the positive sign of the mean velocity value. By contrast, the location of maximum mean velocity for the anterior cerebral artery is at the depth of 67 mm, and the direction of flow is proximal (flowing toward the heart) as indicated by the negative sign of the mean velocity value. The hemodynamic values of the blood flow at these locations can also include the pulsatility indices, which are the difference between peak systolic flow and minimum diastolic flow over a predetermined period of time. Accordingly, the direction and hemodynamic values of the blood flow at the location within each blood vessel of the interconnected blood vessels 306 can be determined from the ultrasound test data 402. Such location-specific data may be stored for use in generating 2D and/or 3D images of the interconnected blood vessels 306 of the brain 308, as described below.

Direction and hemodynamic values of the blood flow may be determined for several locations along the blood vessel 304. Some blood vessels can have substantial variation in blood flow velocity over their length. For example, medial cerebral arteries and basilar arteries can have vessel diameters that vary over their length. Thus, the blood flow velocity can vary substantially over the length of such vessels. In an embodiment, the ultrasound test monitoring system 102 can determined segments of the blood vessel 304, and determine hemodynamic values for each segment. The segment-specific hemodynamic values may be stored for use in generating the 2D and/or 3D images described below.

Figure 5:
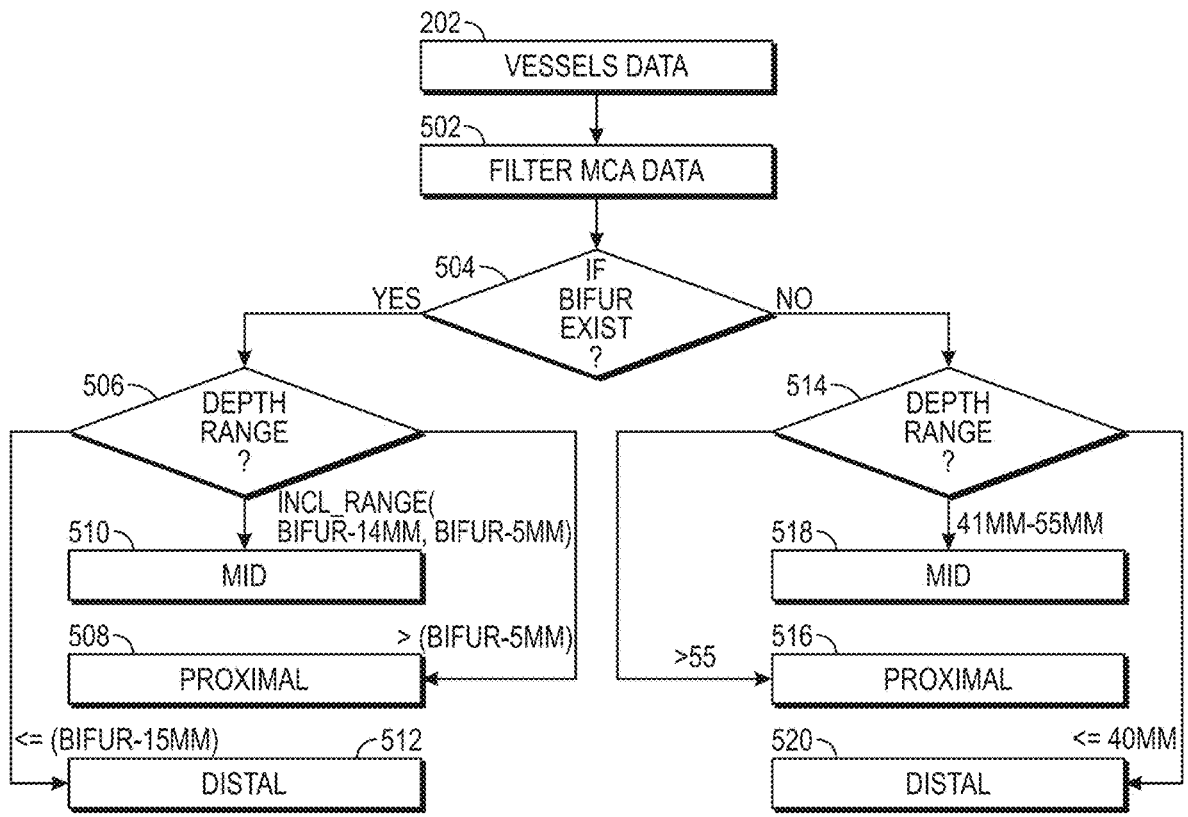
FIG. 5 is a flowchart of a method of determining locations in a blood vessel, in accordance with an embodiment.

Referring to FIG. 5, a flowchart of a method of determining locations in a blood vessel is shown in accordance with an embodiment. The locations in the blood vessel 304 for which direction and hemodynamic values may be reported in the images described below can be determined. The method may be used, for example, to determine locations within a medial cerebral artery.

At operation 202, the ultrasound test data 402 is received. At operation 502, the test data can be filtered to determine a set of test data containing measurements of the medial cerebral artery. Such filtering could, for example, isolate the top two rows of the tabulated data shown in FIG. 4. At operation 504, the ultrasound test monitoring system 102 determines whether a bifurcation 320 (FIG. 3) exists in the test data. The bifurcation 320 can be located at a proximal end of the medial cerebral artery, and thus, may have a maximum depth within the medial cerebral artery relative to the ultrasound probe 302.

At operation 506, the ultrasound test monitoring system 102 determines several segments when the bifurcation 320 is present in the test data. A first segment 508, which may be a proximal segment nearest to the bifurcation 320, can be determined to contain test measurements having depths within a range between a depth of the bifurcation 320 to a first distance, e.g., 5 mm, distal to the bifurcation 320. A second segment 510, which may be a medial segment distal to the proximal segment, can be determined to contain test measurements having depths within a range between the proximal segment to a second distance, e.g., 9 mm, distal to the proximal segment. Accordingly, the medial segment can be between the first distance and the second distance distal to the bifurcation 320. A third segment 512, which may be a distal segment distal to the medial segment, can be determined to contain test measurements having depths within a range distal to the medial segment.

At operation 514, the ultrasound test monitoring system 102 determines several segments when the bifurcation 320 is not present in the test data. A first segment 516, which may be a proximal segment, can be determined to contain test measurements having depths within a range greater than a first distance, e.g., greater than 55 mm, from the ultrasound probe 302. A second segment 518, which may be a medial segment distal to the proximal segment, can be determined to contain test measurements having depths within a range between the proximal segment to a second distance, e.g., between 41-55 mm, from the ultrasound probe 302. Accordingly, the medial segment can be between the first distance and the second distance. A third segment 520, which may be a distal segment distal to the medial segment, can be determined to contain test measurements having depths within a range less than a third distance, e.g., less than 40 mm, from the ultrasound probe 302. Accordingly, the distal segment can be distal to the medial segment.

Figure 6:
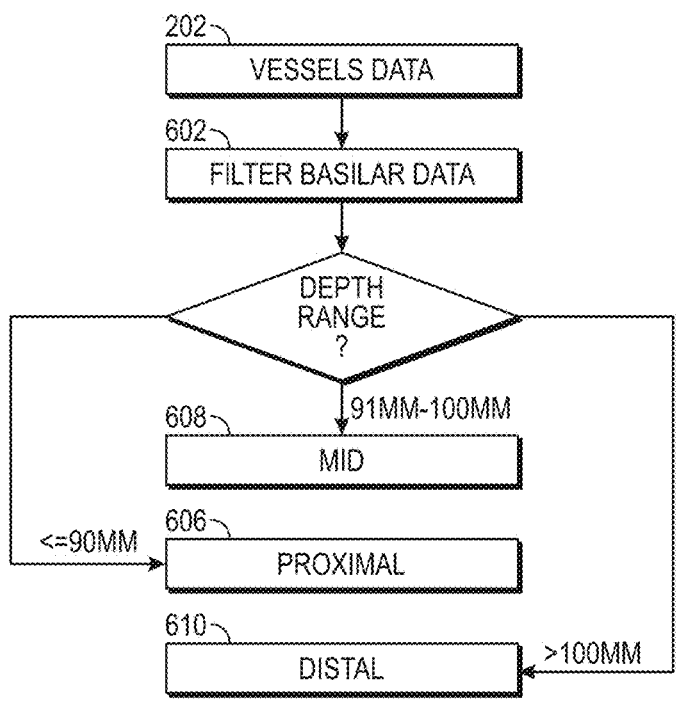
FIG. 6 is a flowchart of a method of determining locations in a blood vessel, in accordance with an embodiment.

Referring to FIG. 6, a flowchart of a method of determining locations in a blood vessel is shown in accordance with an embodiment. The method may be used, for example, to determine locations within a basilar artery.

At operation 202, the ultrasound test data 402 is received. At operation 602, the test data can be filtered to determine a set of test data containing measurements of the basilar artery. At operation 604, the ultrasound test monitoring system 102 determines several segments of the blood vessel 304. A first segment 606, which may be a proximal segment, can be determined to contain test measurements having depths within a range less than a first distance, e.g., less than 90 mm, from the ultrasound probe 302. A second segment 608, which may be a medial segment distal to the proximal segment, can be determined to contain test measurements having depths within a range between the proximal segment to a second distance, e.g., between 91-100 mm, from the ultrasound probe 302. Accordingly, the medial segment can be between the first distance and the second distance. A third segment 610, which may be a distal segment distal to the medial segment, can be determined to contain test measurements having depths within a range greater than a third distance, e.g., greater than 100 mm, from the ultrasound probe 302. Accordingly, the distal segment can be between the second distance and the third distance.

The methods of FIGS. 5 and 6 can establish segments within target vessels of particular types, and other methods may be used for different blood vessel types of the interconnected blood vessels 306. Accordingly, the methods are illustrative and not limiting. In any case, the ultrasound test monitoring system 102 can determine segments of the blood vessel 304 for which direction and/or hemodynamic values are to be determined. For example, the ultrasound test monitoring system 102 can determine respective directions and hemodynamic values, e.g., mean velocity, at locations within each of the proximal segment, medial segment, and distal segment. One location within each segment may be selected. For example, a first location within the proximal segment may be selected based on the first location having a depth 312 that corresponds to a maximum mean velocity measured within the segment. Similarly, a second location 310 within the medial segment may be selected based on the second location having a depth that corresponds to a maximum mean velocity measured within the medial segment, and a third location within the distal segment may be selected based on the third location having a depth that corresponds to a maximum mean velocity measured within the distal segment. The hemodynamic values of the respective locations can be stored for annotating images of the vascular network within the brain 308, as described below.

In an embodiment, the ultrasound test monitoring system 102 determines whether the direction and/or the dynamic values of the location(s) within the blood vessel 304 are normal. Normality can be based on a comparison between the selected test data and predetermined values. For example, the selected test data can be compared to historical data of a general population of patients. The historical data can be processed to establish a normal range for a direction or a hemodynamic value, and the selected test data can be compared to the range to determine whether the value is normal or abnormal at the location in the blood vessel 304.

The historical data of the general population may be measured values from de-identified patients. More particularly, the historical data can be aggregated without including personal data of the patients included in the data set.

Normality of measurements taken for a patient may, in addition or alternatively, be based on a comparison between the selected test data and historical data of the patient. For example, the patient's previous results may be processed to establish a normal range for a direction or a hemodynamic value, and the selected test data can be compared to the range to determine whether the value is normal or abnormal at the location in the blood vessel 304.

The ultrasound test monitoring system 102 can determine whether the direction of blood flow at the location is normal based on whether the direction is distal or proximal in the blood vessel 304. Positive values of mean velocity can indicate blood flow in the distal direction, and negative values of mean velocity can indicate blood flow in the proximal direction. Accordingly, the direction of the blood flow at the location in the blood vessel 304 can be normal when the mean velocity is positive. A reversal of blood flow can ordinarily indicate a stroke or hemorrhage at the location of flow reversal. It will be appreciated, however, that distal or proximal flow directions may occur normally at some locations within the interconnected blood vessels 306. For example, in the distal segment of the medial cerebral artery, blood flow may occasionally reverse due to a curve in the vessel, and thus, a proximal blood flow direction at that location may be normal. Similarly, although basilar arteries may be segmented into three segments, as described above, flow normality may be accurately predicted based on flow in only two of the segments, e.g., the proximal segment and the distal segment, and thus, normality may only be assessed from the predictive segments. Accordingly, the determination of normalcy of the direction of blood flow can depend on both whether the direction is distal or proximal in the blood vessel 304, and the location of the blood flow, e.g., which segment of the blood vessel 304 the flow occurs.

The ultrasound test monitoring system 102 can determine whether the hemodynamic value at the location is normal based on whether the hemodynamic value is within a predetermined normal range. As described above, the predetermined normal range may be based on historical data of the patient and/or of other patients. When the hemodynamic value, e.g., maximum mean velocity or pulsatility index, is within the predetermined normal range, the value is normal. When the hemodynamic value is outside of the predetermined normal range, e.g., is above or below the range, the value is abnormal.

Figure 7:
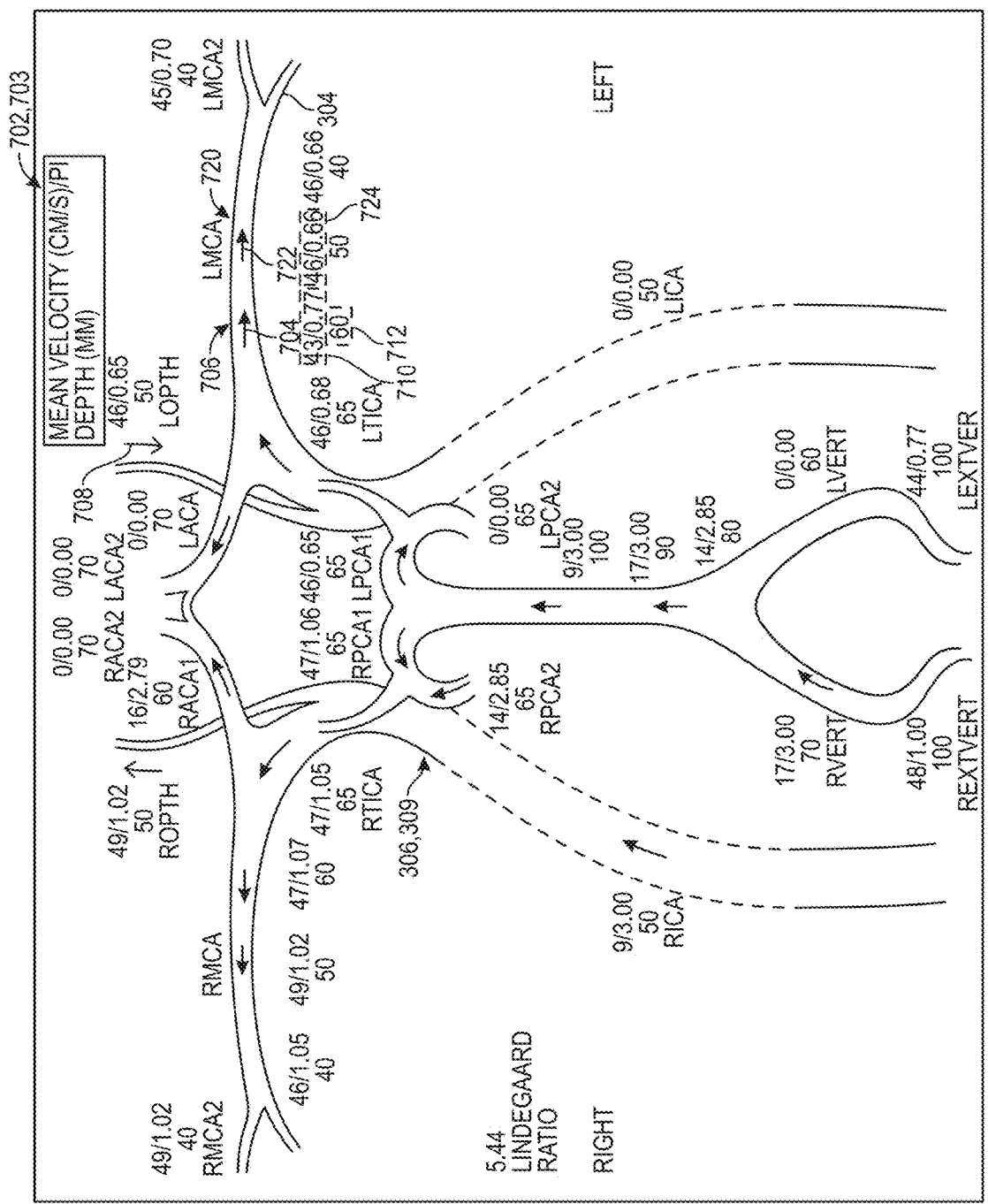
FIG. 7 is a pictorial view of a 2D image of interconnected blood vessels of a brain, in accordance with an embodiment.

Referring to FIG. 7, a pictorial view of a 2D image of interconnected blood vessels of a brain is shown in accordance with an embodiment. At operation 206, the ultrasound test monitoring system 102 generates an image 702 of the interconnected blood vessels 306 of the brain 308. The image 702 can be a 2D image 703 showing a cross-sectional representation of the interconnected blood vessels 306. For example, the interconnected blood vessels 306 can include the circle of Willis 309 and its constituent arteries. Accordingly, the medical practitioner can view at a glance the blood flow anatomy of interest within the brain 308.

In an embodiment, the image 702 includes a direction indicator 704 corresponding to the direction at the respective first location 706 in the respective blood vessel 304. For example, the first location 706 may be within the proximal segment of the medial cerebral artery. The first location 706 may be the location within the proximal segment having the maximum mean velocity. As shown, the maximum mean velocity within the segment can have a positive value, and thus, the direction indicator 704 can be oriented to indicate the direction of blood flow in the distal direction within the blood vessel 304. More particularly, the direction indicator 704 can include an arrow pointing in the distal direction. The orientation of the direction indicator 704 may, however, change based on whether the direction is distal or proximal in the blood vessel 304. For example, as indicated by an abnormal direction indicator 708 associated with the left ophthalmic artery, the direction indicator 704 may be oriented to indicate reverse flow based on the direction in the blood vessel 304 being proximal (abnormally). Accordingly, the orientation of the direction indicator 704 may be based on whether the direction is distal or proximal in the blood vessel 304.

As described above, direction indicators 704 may not accompany every vessel segment. For example, for both the right and left medial cerebral arteries, direction indicators 704 may be displayed only for the proximal segment and the medial segment. More particularly, the distal segment of the medial cerebral arteries may not have an associated direction indicator 704. Similarly, with respect to basilar arteries, direction indicators 704 may only be displayed for the distal segment and the proximal segment, but not the medial segment. In the event that hemodynamic values are captured for only one segment of the blood vessel 304, the image 702 may display the direction indicator at a position that is in a middle of the blood vessel 304. More particularly, the single direction indicator can be located at a longitudinal midpoint along the blood vessel 304 irrespective of a depth at which the hemodynamic value is captured.

The generated image 702 can include a hemodynamic indicator 710 corresponding to one or more of the hemodynamic values determined for the first location. More particularly, the hemodynamic indicators 710 can include one or more hemodynamic values providing information about the blood flow at the first location. The hemodynamic values can be measured or calculated values based on the ultrasound test data 402. For example, the hemodynamic values included in the hemodynamic indicators 710 can be one or more of a mean velocity of the blood flow at the first location 706 in the blood vessel 304, or a pulsatility index of the blood flow at the location of the blood vessel 304. The values can be grouped together and positioned near the direction indicator 704. For example, the direction indicator 704 may be overlaid on the blood vessel 304 at a position within a lumen of the blood vessel 304, and the hemodynamic indicator 710 can be positioned adjacent to the blood vessel 304, e.g., immediately outside of a vessel wall of the blood vessel 304.

As described above, the displayed location can correspond to a maximum mean velocity. The maximum mean velocity may be an absolute value, meaning that the mean velocity value may be positive (distal flow) or negative (proximal flow), and will be the maximum value if it has the largest absolute value. Similarly, the hemodynamic indicators can include the pulsatility index at the displayed location. The hemodynamic indicators may include other information about the blood vessel 304 and/or the blood flow within the blood vessel 304. Accordingly, the hemodynamic indicators can include information about the blood flow within the vessel segment of interest, which can be quickly reviewed by the medical practitioner and used to assess whether the blood flows normal.

In an embodiment, the image 702 includes a depth indicator 712. The depth indicator 712 corresponds to a depth to the location, e.g., the first location 706, from the ultrasound probe 302 used to generate the ultrasound test data 402. For example, the depth indicator 712 can include a value of the depth, e.g., 60 mm, that can be quickly reviewed by the medical practitioner and used to assess the depth at which the blood flow characteristics shown in the image exist.

The image 702 can include respective direction indicators and hemodynamic indicators for each vessel segment. For example, as described above, the ultrasound test monitoring system 102 can determine, based on the ultrasound test data 402, the direction and hemodynamic values of several segments of the medial cerebral artery. In an embodiment, the image 702 includes, at a second location 720 in the blood vessel 304, a second direction indicator 722 corresponding to the second direction calculated for the segment, and a second hemodynamic indicator 724 corresponding to the one or more second hemodynamic values measured or calculated for the segment. Similar to the indicators associated with the first location 706, indicators associated with the second location 720 can provide information about the direction and flow characteristics at the location having a maximum mean velocity within the vessel segment.

The indicators of the image 702 can be displayed to indicate normality or abnormality of the represented metric. For example, as described above, an orientation of the direction indicator 704 can indicate a direction of the blood flow at the location 706, and thus, whether the blood flow is normally directed. Similarly, a color of the indicators may indicate normality or abnormality. For example, a color of the hemodynamic indicators 710 may be based on whether the one or more hemodynamic values grouped in the indicator is within a predetermined normal range. More particularly, if one of the hemodynamic values, e.g., the maximum mean velocity, is within the predetermined normal range, the value may be indicated in a first color, e.g., black. By contrast, if the hemodynamic value is outside of the predetermined normal range, value may be indicated in a second color, e.g., red. Other modes of indicating abnormality may be used, such as animating the indicator, e.g., causing the indicator to blink.

The image 702 can include other indicators such as names of the vessels. The names may be overlaid on the image 702 adjacent to the corresponding vessel. The image 702 may also indicate hemodynamic information about the interconnected blood vessels 306. For example, a Lindegaard ratio of the interconnected blood vessels 306 may be shown in the image 702. The Lindegaard ratio refers to a calculated ratio of the mean flow velocity in the middle cerebral artery and the ipsilateral extracranial internal carotid artery, and can be used by the medical practitioner to assess the presence of vasospasm.

The 2D image 703 containing the circle of Willis 309 with annotated blood flow values can provide an efficient mode of assessing blood flow health. In an embodiment, the medical practitioner may desire more information than what is provided on the face of the image 702. Accordingly, the ultrasound test monitoring system 102 can generate an interactive image to allow the medical practitioner to easily navigate through images or videos associated with the hemodynamic indicators. More particularly, as described below, one or more of the direction indicators or the hemodynamic indicators may be selectable to cause display of a graphical object representing the blood flow at the designated location.

Figure 8:
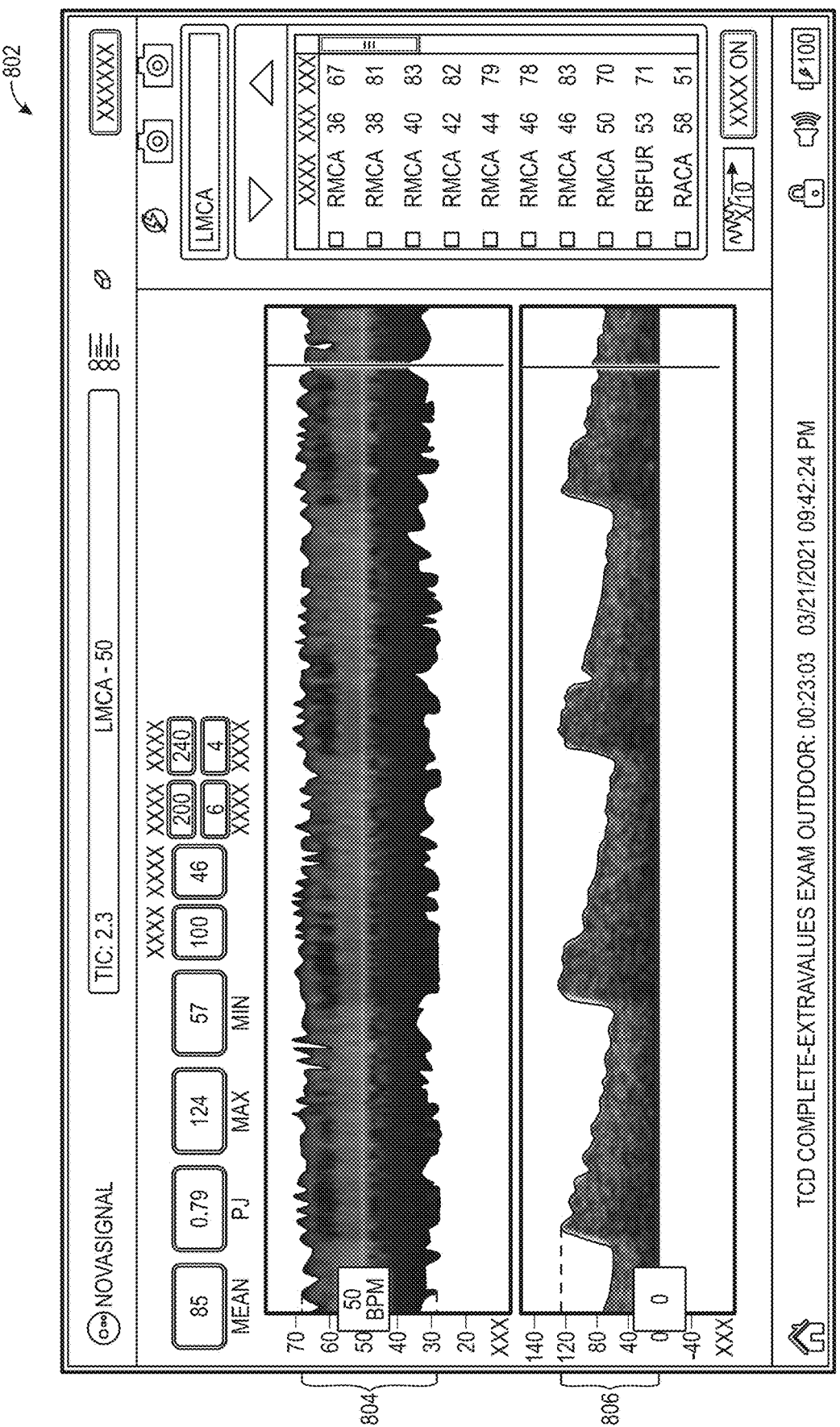
FIG. 8 is a pictorial view of a graphical object representing blood flow at a location in a blood vessel, in accordance with an embodiment.

Referring to FIG. 8, a pictorial view of a graphical object representing blood flow at a location in a blood vessel is shown in accordance with an embodiment. The direction indicator 704 may be selectable to cause display of a graphical object 802 including additional information about the blood flow at the location 706 associated with the direction indicator 704. For example, the graphical object 802 can include one or more charts of the blood flow at the location 706.

A first chart 804 can include M-mode data. The M-mode data can include time motion display of the ultrasound wave as it propagates through the neurovasculature. A second chart 806 can represent blood flow velocity at a selected depth relative to the M-mode data. More particularly, the waveform of the second chart 806 can show cerebral blood flow velocity (CBFV), which increases and decreases as the blood pressure within the neurovasculature oscillates. Accordingly, the first chart 804 can show Doppler over time, and the second chart 806 can include calculations of cerebral blood flow velocity. In addition to the raw and calculated data shown in the chart(s), derived data can be calculated to represent characteristics of the blood flow. For example, the mean blood velocity, maximum blood velocity, minimum blood velocity, and pulsatility index at the location 706 can be displayed in the blood flow image 802 that is launched upon selection of the direction indicator 704.

Figure 9:
FIG. 9 is a pictorial view of a graphical object representing blood flow at a location in a blood vessel, in accordance with an embodiment.

Referring to FIG. 9, a pictorial view of a graphical object representing blood flow at a location in a blood vessel is shown in accordance with an embodiment. The hemodynamic indicators 710 may be selectable to cause display of a graphical object 802 including additional information about the blood flow at the location 706 associated with the direction indicator 704. For example, the graphical object 802 can include audiovisual content detailing the hemodynamic information associated with the measured location. The information can include, among other details, a vessel name, a depth to the location of interest, a mean velocity of blood flow at the location of interest, a pulsatility index of blood flow at the location of interest, a maximum velocity of blood flow at the location of interest, a minimum velocity of blood flow at the location of interest, etc. The audiovisual content may also include an image and/or a video captured during the ultrasound exam. Selectable buttons may be included in the graphical object 802 to allow the medical practitioner to move to a previous or next entry, e.g., blood flow values at other depths along the blood vessel of interest. The medical practitioner can efficiently review the depth and details of measurements to be assured that the blood flow values represented in the image 702, e.g., overlaid beside the vessel graphic, are correct.

Dynamic images may also include animation to convey information to the medical practitioner. In an embodiment, the direction indicator 704 can be animated to represent flow direction and velocity within the blood vessel 304. For example, instead of or in addition to an arrow, the direction indicator 704 can include lines, dots, or other animated features that move through the vessel. The movement of the animated features, e.g., a speed at which the features move, can correspond to the hemodynamic values captured for the location of interest. For example, when the maximum mean velocity of the proximal segment of a vessel is larger than the maximum mean velocity of the distal segment of the vessel, the rendered animated features can move through the proximal segment at a faster rate than the animated features move through the distal segment. The difference in speed of the animated features can aid in visualizing how blood accelerates or decelerates within the blood vessel 304.

Figure 10:
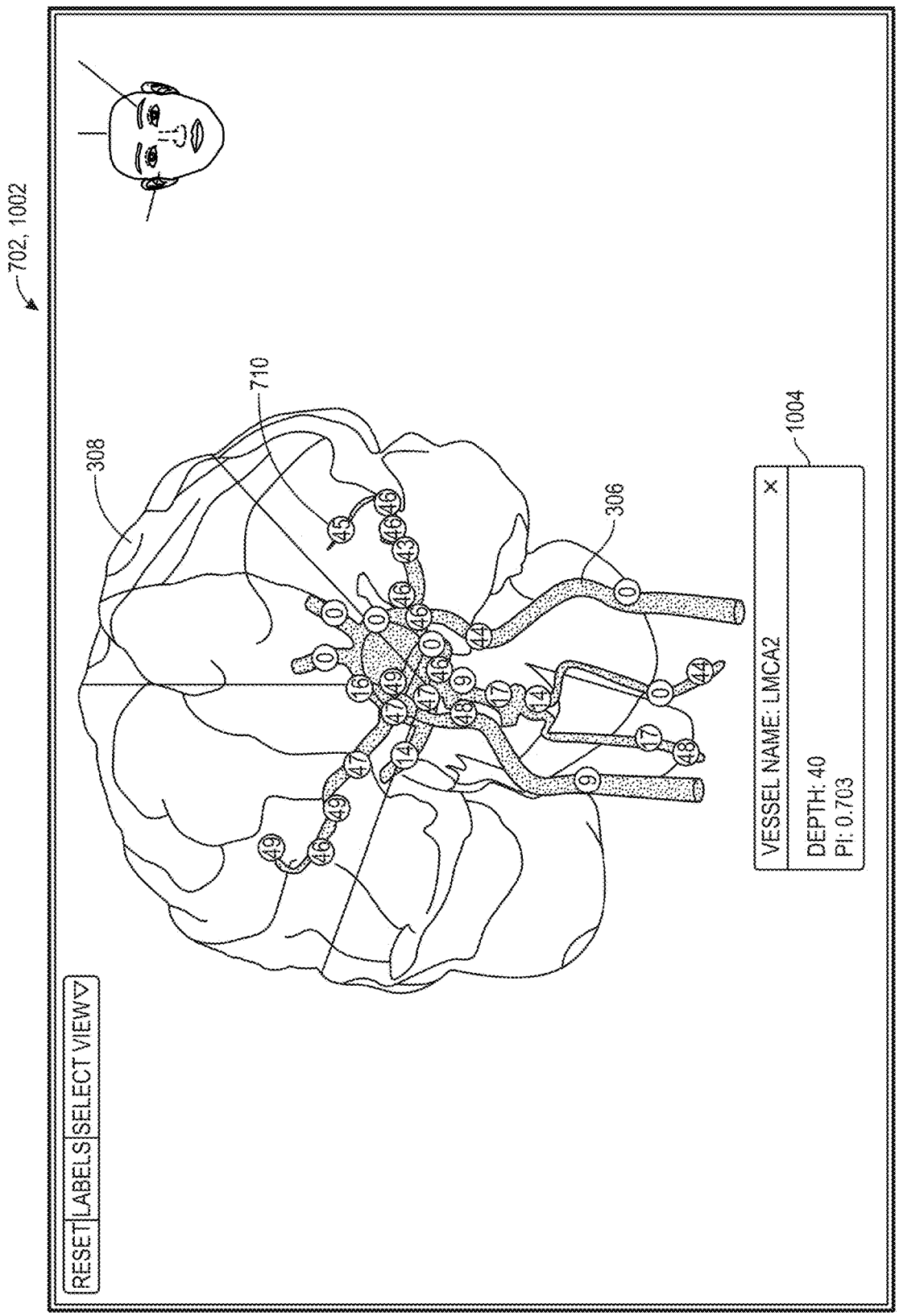
FIG. 10 is a pictorial view of a 3D image of interconnected blood vessels within a brain, in accordance with an embodiment.

Referring to FIG. 10, a pictorial view of a 3D image of interconnected blood vessels within a brain is shown in accordance with an embodiment. The generated image 702 can be a 3D image 1002 of the interconnected blood vessels 306 within the brain 308. More particularly, the generated image 702 can have a 3D representation of a brain 308, and the interconnected blood vessels 306 can be overlaid on the brain 308. An orientation of the brain 308 and the interconnected blood vessels 306 can match such that the 3D model gives a more realistic visualization (compared to the 2D image 703) of the circle of Willis 309, as it relates to the brain structure.

In an embodiment, the 3D image 1002 can be annotated with any of the information described above with respect to the 2D image 703. For example, hemodynamic indicators 710 may be overlaid on the vasculature at respective positions corresponding to locations of measurement within the vasculature. The hemodynamic indicators can include labels having a value, e.g., a maximum mean velocity at the location. The medical practitioner can change the metric displayed on the 3D image 1002 through user selectable settings. For example, the hemodynamic indicators 710 may be changed to show the pulsatility index, a name of the vessel, etc. In an embodiment, such values may be shown on a same view. For example, a user selection of the hemodynamic indicators 710, e.g., a tap or a click, can cause a detail view 1004 to launch within the 3D image 1002. The detail view 1004 can provide additional information about the corresponding location, e.g., a vessel name, a depth, a pulsatility index, etc.

The image 702, e.g., the 2D image 703 or the 3D image 1002, may be a static image. More particularly, information displayed in the image 702 may not move upon presentation. Alternatively, the information may be displayed dynamically. For example, the direction indicator 704 and hemodynamic indicators 710 may be updated in real-time as ultrasound test data 402 is streamed from the TCD ultrasound machine 106 to the ultrasound test monitoring system 102. By way of example, test data may be updated every 50 milliseconds, and thus, the ultrasound test monitoring system 102 can update the image 702 as the new data is received and processed. In an embodiment, a dynamic image can have indicators, e.g., arrows and/or hemodynamic values, that update every 1-10 seconds, e.g., every 2 seconds. Accordingly, the image 702 can be reviewed by a medical practitioner for real-time monitoring of the patient under examination.

In an embodiment, the 3D image 1002 can be manipulated to change an orientation of the brain and the vasculature. For example, an icon of a head may be located in a corner of the image 702. Selection and rotation of the head icon, e.g., using keystrokes of an alphanumeric input device or clicking and dragging the icon using a cursor control device, can cause the rendering of the brain and the vasculature to rotate similarly. Accordingly, the medical practitioner can manipulate the view of the brain and the vasculature to more easily view different vessels and to facilitate explaining the blood flow characteristics to others.

Figure 11:
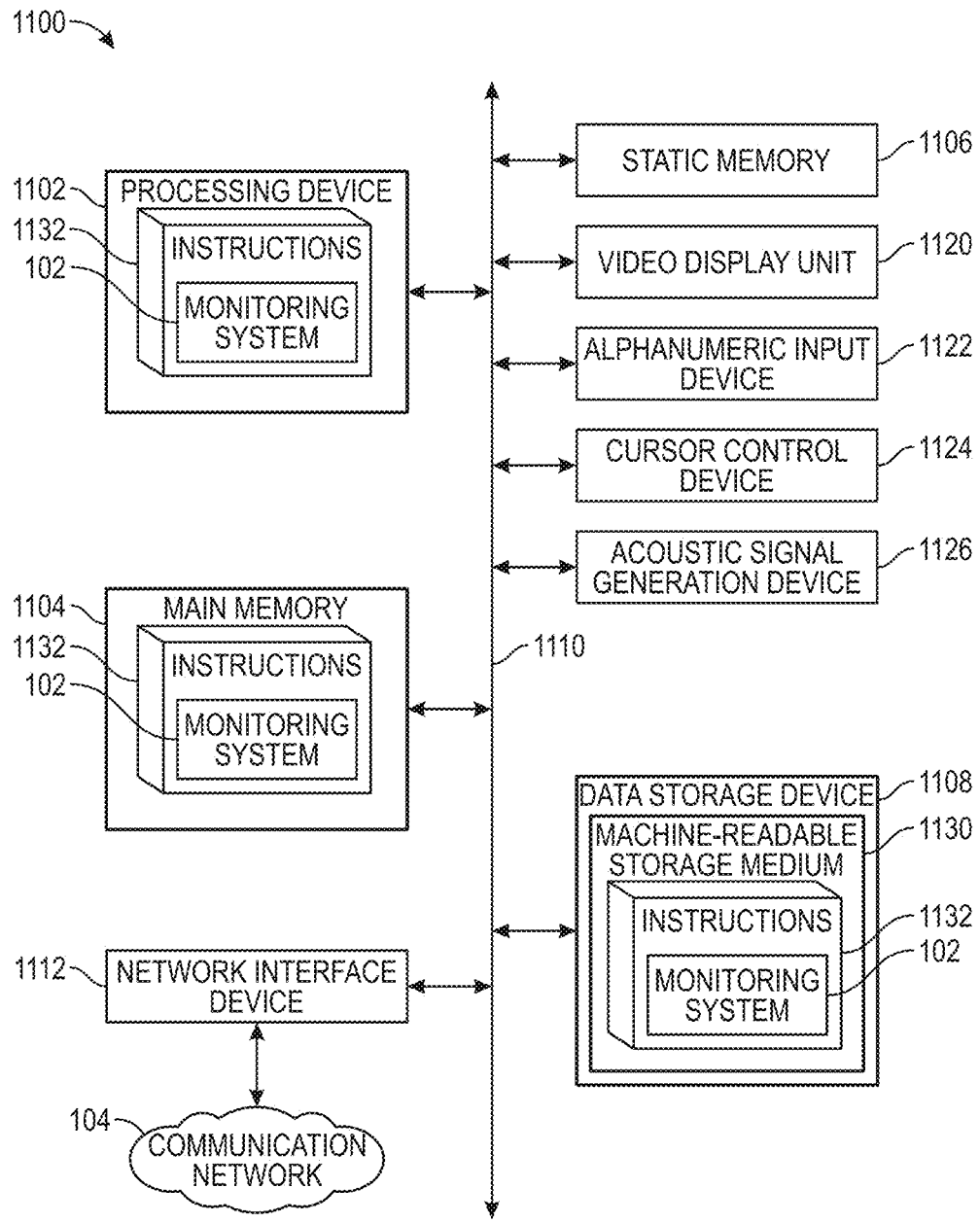
FIG. 11 is a block diagram of an example computing device that may perform one or more of the operations described herein, in accordance with an embodiment.

Referring to FIG. 11, a block diagram of an example computing device that may perform one or more of the operations described herein is shown in accordance with an embodiment. The ultrasound test monitoring system 102 (and/or TCD machine 106 or user device 108) may include one or more computing devices 1100. Computing device 1100 may be connected to other computing devices in a LAN, an intranet, an extranet, and/or the Internet. The computing device may operate in the capacity of a server machine, e.g., computing system, or a client machine, e.g., remote client device, in a client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. In some embodiments, while only a single computing device is illustrated, the term "computing device" may be taken to include any collection of computing devices that individually or jointly execute a set (or multiple sets) of instructions to perform the methods discussed herein.

The example computing device 1100 may include one or more processing devices (e.g., a general purpose processor, a PLD, etc.) 1102, a main memory 1104 (e.g., synchronous dynamic random access memory (DRAM), read-only memory (ROM)), a static memory 1106 (e.g., flash memory) and a data storage device 1108, which may communicate with each other via a bus 1110.

Processing device 1102 may be provided by one or more general-purpose processing devices such as a microprocessor, central processing unit, or the like. In an illustrative example, processing device 1102 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1102 may comprise one or more special-purpose processing devices such as an application specific integrated circuit (ASIC), a field programmable gate array (FPGA), a digital signal processor (DSP), network processor, or the like. The processing device(s) 1102 may be configured to execute the operations described herein, in accordance with one or more aspects of the present disclosure, for performing the operations and steps discussed herein.

Computing device 1100 may include a network interface device 1112 which may communicate with a communication network 104. The computing device 1100 may include a video display unit 1120 (e.g., a liquid crystal display (LCD) or a cathode ray tube (CRT)), an alphanumeric input device 1122 (e.g., a keyboard), a cursor control device 1124 (e.g., a mouse) and an acoustic signal generation device 1126 (e.g., a speaker). In one embodiment, video display unit 1120, alphanumeric input device 1122, and cursor control device 1124 may be combined into a single component or device (e.g., an LCD touch screen).

Data storage device 1108 may include a non-transitory computer-readable storage medium 1130 on which may be stored one or more sets of instructions 1132 that may include instructions for one or more components (e.g., one or more of the components or microservices of the ultrasound test monitoring system) for carrying out the operations described herein, in accordance with one or more aspects of the present disclosure. For example, instructions for the monitoring system 102 are illustrated by way of example, and not limitation. Instructions 1132 may reside, completely or at least partially, within main memory 1104 and/or within processing device 1102 during execution thereof by computing device 1100, main memory 1104 and processing device 1102 constituting computer-readable media. The instructions 1132 may be transmitted or received over the communication network 104 via network interface device 1112.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method, comprising:
   receiving ultrasound test data representing blood flow in a blood vessel of a plurality of interconnected blood vessels of a brain;
   filtering the ultrasound test data to obtain first blood vessel data associated with a first blood vessel;
   determining, based on the first blood vessel data, a first direction and one or more first hemodynamic values of the blood flow at a first location of the first blood vessel;
   generating, based on the ultrasound test data, a first interactive image of the plurality of interconnected blood vessels of the brain, wherein the first interactive image includes a first direction indicator corresponding to the first direction and a first hemodynamic indicator corresponding to the one or more first hemodynamic values at the first location of the first blood vessel, wherein the first direction indicator is configured to receive a selection from a user of the first interactive image;
   determining a user selection of the first direction indicator within the first interactive image; and
   in response to determining the user selection, generating, based on the first blood vessel data, a second interactive image different from the first interactive image, wherein the second interactive image includes a graphical indicator, different from the first direction indicator and the first hemodynamic indicator, corresponding to the one or more first hemodynamic values of the blood flow at the first location over time.

2. The method of claim 1, wherein the one or more first hemodynamic values includes one or more of a mean velocity of the blood flow at the first location in the blood vessel or a pulsatility index of the blood flow at the first location in the blood vessel.

3. The method of claim 1, wherein the first interactive image includes a depth indicator corresponding to a depth to the first location from an ultrasound probe used to generate the ultrasound test data.

4. The method of claim 1, wherein an orientation of the first direction indicator is based on whether the direction is distal or proximal in the blood vessel.

5. The method of claim 1, wherein a color of the first hemodynamic indicator is based on whether the one or more first hemodynamic values is within a predetermined normal range.

6. The method of claim 1, further comprising:
   determining, based on the ultrasound test data, a second direction and one or more second hemodynamic values of the blood flow at a second location in the blood vessel, wherein the first interactive image includes a second direction indicator corresponding to the second direction and a second hemodynamic indicator corresponding to the one or more second hemodynamic values.

7. The method of claim 1, wherein the first image is a 2D image of the plurality of interconnected blood vessels of the brain.

8. The method of claim 1, wherein the first image is a 3D image of the plurality of interconnected blood vessels within the brain.

9. The method of claim 1, wherein the plurality of interconnected blood vessels includes a circle of Willis of the brain.

10. A non-transitory computer readable medium containing instructions, which when executed by one or more processors of an ultrasound test monitoring system, cause the ultrasound test monitoring system to perform a method, comprising:
  receiving ultrasound test data representing blood flow in a blood vessel of a plurality of interconnected blood vessels of a brain;
  filtering the ultrasound test data to obtain first blood vessel data associated with a first blood vessel;
  determining, based on the first blood vessel data, a first direction and one or more first hemodynamic values of the blood flow at a first location of the first blood vessel;
  generating, based on the ultrasound test data, a first interactive image of the plurality of interconnected blood vessels of the brain, wherein the first interactive image includes a first direction indicator corresponding to the first direction and a first hemodynamic indicator corresponding to the one or more first hemodynamic values at the first location of the first blood vessel, wherein the first direction indicator is configured to receive a selection from a user of the first interactive image;
  determining a user selection of the first direction indicator within the first interactive image; and
  in response to determining the user selection, generating, based on the first blood vessel data, a second interactive image different from the first interactive image, wherein the second interactive image includes a graphical indicator, different from the first direction indicator and the first hemodynamic indicator, corresponding to the one or more first hemodynamic values of the blood flow at the first location over time.

11. The non-transitory computer readable medium of claim 10, wherein the one or more first hemodynamic values includes one or more of a mean velocity of the blood flow at the first location in the blood vessel or a pulsatility index of the blood flow at the first location in the blood vessel.

12. The non-transitory computer readable medium of claim 10, wherein the first interactive image includes a depth indicator corresponding to a depth to the first location from an ultrasound probe used to generate the ultrasound test data.

13. The non-transitory computer readable medium of claim 10, wherein the method further comprises:
  determining, based on the ultrasound test data, a second direction and one or more second hemodynamic values of the blood flow at a second location in the blood vessel, wherein the first interactive image includes a second direction indicator corresponding to the second direction and a second hemodynamic indicator corresponding to the one or more second hemodynamic values.

14. The non-transitory computer readable medium of claim 10, wherein the first image is a 2D image of the plurality of interconnected blood vessels of the brain.

15. The non-transitory computer readable medium of claim 10, wherein the first image is a 3D image of the plurality of interconnected blood vessels within the brain.

16. An ultrasound test monitoring system, comprising:
  a memory configured to store ultrasound test data representing blood flow in a blood vessel of a plurality of interconnected blood vessels of a brain; and
  one or more processors configured to
    receive the ultrasound test data;
    filter the ultrasound test data to obtain first blood vessel data associated with a first blood vessel;
    determine, based on the first blood vessel data, a first direction and one or more first hemodynamic values of the blood flow at a first location of the first blood vessel;
    generate, based on the ultrasound test data, a first interactive image of the plurality of interconnected blood vessels of the brain, wherein the first interactive image includes a first direction indicator corresponding to the first direction and a first hemodynamic indicator corresponding to the one or more first hemodynamic values at the first location of the first blood vessel, wherein the first direction indicator is configured to receive a selection from a user of the first interactive image;
    determine a user selection of the first direction indicator within the first interactive image; and
    in response to determining the user selection, generate, based on the first blood vessel data, a second interactive image different from the first interactive image, wherein the second interactive image includes a graphical indicator, different from the first direction indicator and the first hemodynamic indicator, corresponding to the one or more first hemodynamic values of the blood flow at the first location over time.

17. The ultrasound test monitoring system of claim 16, wherein the one or more first hemodynamic values includes one or more of a mean velocity of the blood flow at the first location in the blood vessel or a pulsatility index of the blood flow at the first location in the blood vessel.

18. The ultrasound test monitoring system of claim 16, wherein the first interactive image includes a depth indicator corresponding to a depth to the first location from an ultrasound probe used to generate the ultrasound test data.

19. The ultrasound test monitoring system of claim 16, wherein the one or more processors are further configured to:
  determine, based on the ultrasound test data, a second direction and one or more second hemodynamic values of the blood flow at a second location in the blood vessel, wherein the first interactive image includes a second direction indicator corresponding to the second direction and a second hemodynamic indicator corresponding to the one or more second hemodynamic values.

20. The ultrasound test monitoring system of claim 16, wherein the first image is a 2D image of the plurality of interconnected blood vessels of the brain.

* * * * *